(12) United States Patent
Ching-Hsiang et al.

(10) Patent No.: US 7,351,572 B2
(45) Date of Patent: Apr. 1, 2008

(54) **MICROORGANISM STRAIN GM-090 OF *LACTOBACILLUS FERMENTUM* AND ITS USE FOR STIMULATING IFN-γ SECRETION AND/OR TREATING ALLERGY**

(75) Inventors: Hsu Ching-Hsiang, Tainan County (CN); Ying-Jen Lu, Tainan County (CN)

(73) Assignee: GenMont Biotech Inc. (TW)

( * ) Notice: Subject to any disclaimer, the term of this patent is extended or adjusted under 35 U.S.C. 154(b) by 278 days.

(21) Appl. No.: 10/965,109

(22) Filed: Oct. 15, 2004

(65) Prior Publication Data

US 2006/0083723 A1  Apr. 20, 2006

(51) Int. Cl.
C12N 1/20 (2006.01)
C12N 1/00 (2006.01)
A01N 63/00 (2006.01)

(52) U.S. Cl. .................. 435/252.9; 435/853; 424/93.45

(58) Field of Classification Search ............. 435/252.9, 435/853; 424/93.45
See application file for complete search history.

(56) References Cited

U.S. PATENT DOCUMENTS 6,066,343 A * 5/2000 Megeed et al. ............... 426/20

FOREIGN PATENT DOCUMENTS

| EP | 1 555 028 A1 | 7/2005 |
|---|---|---|
| WO | WO 02/45727 | * 6/2002 |

OTHER PUBLICATIONS

Townley, RG and Okada, C. Annals of Allergy, 68:190-196, 1992.
Sareneva T. et al. "Infuenza A virus-induced IFN-α/βand IL-18 synergistically enhance IFN-γ gene expression in human T cells," *J Immunol* 160:6032-6038, 1998.
Shida K. et al., "*Lactobacillus casei* inhibits antigen-induced IgE secretion through regulation of cytokine production in murine splenocyte culture," *Int Arch Allergy Immunol* 115:278-287, 1998.
Blum S. et al., "Intestinal microflora and the interaction with immunocompetent cells," *Antonie Van Leeuwenhoek* 76:199-205, 1999.
Contractor NV et al. "Lymphoid hyperplasia, autoimmunity and compromised intestinal intraepithelial lymphocyte development in colits-free gnotobiotic IL-2deficient mice," *J Immunol* 160:385-394, 1998.
Haller D. et al. "Non-pathogenic bacteria elicit a different cytokine response by intestinal epithelial ceel/leucocyte co-culture," *Gut* 47:79-87, 2000.
Arunachalam K. et al., "Enhancement of natural immune function by dietary consumption of *Bifidobacterium lac/is* (HN 019)," *Eur J Clin Nutr* 54:263-267, 2000.
Kishi A. et al., "Effect of the oral administration of *Lactobacillus brevis* subsp. Coagulans on interferon-a producing capacity in humans," *J Am Coli Nutr* 15:408412, 1996.
Pouwels, P.H. et al., "The potential of Lactobacillus as a carrier for oral immunization: development and preliminary characterization of vector systems for targeted delivery of antigens," *J Biotechnol* 44: 183-92, 1996.
Kalliomaki, M. et al., "Probiotics and prevention of atopic disease: 4year follow-up of a randomised placebo-controlled trial," *Lancet* 361(9372):186971, 2003.
Kirjavainen, P. V. et al., "Probiotic bacteria in the management of atopic disease: underscoring the importance of viability," *J Pediatr Gastroenterol Nutr* 36(2): 223-7, 2003.
Dreborg, S. "The implications of nomenclature," *Ann Allergy Asthma Immunol* 89(6 Suppl 1):83-5, 2002.
Pessi, T. et al. "Interleukin-IO generation in atopic children following oral *Lactobacillus rhamnosus* GG," *Clin Exp Allergy* 30(12): 1804-8, 2000.
Isolauri, E.T. et al. "Probiotics in the management of atopic eczema,"*Clin Exp Allergy* 30(11): 1604-10,2000.
Yeung, P.S.M. et al., "Species-specific Identification of Commercial Probiotic Strains," *J Diary Sci.* 85:1039-1051, 2002.
van Beek, S. and Pries, F. G. "Evolution of the lactic acid bacterial community during malt whisky fermentation: a polyphasic study," *Appl Environ Microbiol* 68(1): 297-305, 2002.
Simpson, K. L. et al. "Characterization of lactobacilli from Scotch malt whisky distilleries and description of *Lactobacillus ferintoshensis* sp. nov., a new species isolated from malt whisky fermentations," *Microbiology* 147:1007-1016, 2001.
Jackson, D. E. et al., "Induction of hypersensitivity reactions to *Lactobacillus fermentum* and lipoteichoic acid in rabbits. Part II," *Int Arch Allergy Appl Immunol* 65(3): 304-12, 1981.
Jackson, D. E. et al., "Induction of IgM immunological memory to lipoteichoic acids in rabbits. Part I," *Int Arch Allergy Appl Immunol* 65(2):198-202, 1981.
Jackson, D. E. et al., "Immune responses to lipoteichoic acid: comparison of antibody responses in rabbits and mice. Part II," *Int Arch Allergy Appl Immunol* 65(2):203-11, 1981.
Ishida, Y. et al., "Decrease in ovalbumin specific IgE of mice serum after oral uptake of lactic acid bacteria," *Biosci Biotechnol Biochem* 67(5):951-957, 2003.
Angelis, M.D. et al., "Characterization of Non-Starter Lactic Acid Bacteria from Italian Ewe Cheeses Based on Phenotypic, Genotypic, and Cell Wall Protein Analyses," *Appl. Environ. Microbiol.* 67: 2011-2020, 2001.
Plant, L. and Conway, P., "Association of *Lactobacillus* spp. with Peyer's Patches in Mice," *Appl Environ Microbiol* 8(2):320-324, 2001.
De Ruiz, C.S. et al., "Experimental Administration of Estradiol on the Colonization of *Lactobacillus.termentum* and *Escherichia coli* in the Urogenital Tract of Mice,"*Biol. Pharm. Bull.* 24(2):127-134, 2001.

* cited by examiner

Primary Examiner—Vera Afremova
(74) *Attorney, Agent, or Firm*—Banner & Witcoff, Ltd.

(57) ABSTRACT

The present invention provides an isolated microorganism strain, *Lactobacillus fermentum* GM-090, which is found to be effective in stimulating IFN-γ secretion and/or treating allergy. The use of the *Lactobacillus fermentum* GM-090 in stimulating IFN-γ secretion and/or treating allergy is also provided.

7 Claims, 8 Drawing Sheets

SEQUENCE LISTING

```
<160> NUMBER OF SEQ ID NOS: 5

<210> SEQ ID NO 1
<211> LENGTH: 510
<212> TYPE: DNA
<213> ORGANISM: Lactobacillus fermentum
<220> FEATURE:
<221> NAME/KEY: misc_feature
<222> LOCATION: (498)..(498)
<223> OTHER INFORMATION: n is a, c, g, or t

<400> SEQUENCE: 1
cgaacgcgtt ggcccaattg attgatggtg cttgcacctg attgattttg gtcgccaacg      60
agtggcggac gggtgagtaa cacgtaggta acctgcccag aagcggggga caacatttgg     120
aaacagatgc taataccgca taacaacgtt gttcgcatga acaacgctta aaagatggct     180
tctcgctatc acttctggat ggacctgcgg tgcattagct tgttggtggg gtaacggcct     240
accaaggcga tgatgcatag ccgagttgag agactgatcg gccacaatgg gactgagaca     300
cggcccatac tcctacggga ggcagcagta gggaatcttc cacaatgggc gcaagcctga     360
tggagcaaca ccgcgtgagt gaagaagggt ttcggctcgt aaagctctgt tgttaaagaa     420
gaacacgtat gagagtaact gttcatacgt tgacggtatt taaccagaaa gtcacggcta     480
actacgtgcc agcagcgngg gttaatacaa                                     510

<210> SEQ ID NO 2
<211> LENGTH: 20
<212> TYPE: DNA
<213> ORGANISM: Artificial
<220> FEATURE:
<223> OTHER INFORMATION: primer

<400> SEQUENCE: 2
agagtttgat cctggctcag                                                  20

<210> SEQ ID NO 3
<211> LENGTH: 18
<212> TYPE: DNA
<213> ORGANISM: Artificial
<220> FEATURE:
```

-continued

```
<223> OTHER INFORMATION: primer

<400> SEQUENCE: 3
gtattaccgc ggctgctg                                                 18

<210> SEQ ID NO 4
<211> LENGTH: 10
<212> TYPE: DNA
<213> ORGANISM: Artificial
<220> FEATURE:
<223> OTHER INFORMATION: primer

<400> SEQUENCE: 4
atgtaacgcc                                                          10

<210> SEQ ID NO 5
<211> LENGTH: 9
<212> TYPE: DNA
<213> ORGANISM: Artificial
<220> FEATURE:
<223> OTHER INFORMATION: primer

<400> SEQUENCE: 5 ctgcggcat                                                            9
```

MICROORGANISM STRAIN GM-090 OF LACTOBACILLUS FERMENTUM AND ITS USE FOR STIMULATING IFN-γ SECRETION AND/OR TREATING ALLERGY

BACKGROUND OF THE INVENTION

1. Field of the Invention

The invention mainly relates to a novel microorganism strain, Lactobacillus fermentum GM-090 and its use for stimulating IFN-γ secretion and/or treating allergy.

2. Description of the Related Art

Allergy refers to an acquired potential to develop immunologically mediated adverse reaction to normally innocuous substances. Allergic reaction provokes symptoms such as itching, coughing, wheezing, sneezing, watery eyes, inflammation and fatigue. It is believed that allergic reaction includes an early specific immune response and a late inflammatory reaction. It was reported that allergens (e.g. pollens and mite dust) mediated the early phase of allergy by stimulating high affinity immunoglobulin (IgE) receptors. For instance, mast cells and basophils, when stimulated by allergens, would release histamine and cytokines. The cytokines released from mast cells and basophils then mediated the late phase of allergy by recruiting inflammatory cells (see Serafin, W E, In Goodman and Gillmans, "The Pharmacological Basis of Therapeutics", Hardmen, Ja; Limbird, L, E eds, McGraw-Hill, N.Y., 659-682, 1996). It was also reported that the influx of eosinophils, macrophages, lymphocytes, neutrophils and platelets started the vicious inflammatory cycle. The late phase of allergy amplified the initial immune response, which in turn triggered the release of more inflammatory cells (Townley, R G and Okada, C, Annals of Allergy, 68: 190-196, 1991).

Various therapies have been pursued in order to treat the symptoms of allergies. Among them, anti-allergics and histamine H-receptor antagonists (anti-histamines) have been used. Histamine antagonists were administered to antagonize the action of histamine released from mast cells in response to the presence of allergens. They reduced the redness, itching and swelling caused by the action of histamine on the target tissues, and served to prevent or alleviate many of the symptoms resulting from degranulation of mast cells. However, anti-histamines were also reported to be associated with adverse reactions such as diminished alertness, slowed reaction times and somnolence (Goodman and Gillman, The Pharmacological Basis of Therapeutics, Eighth Edition, Pergamon Press, New York, pages 575-588, 1990).

There are also some reports on the treatment of allergies by regulating cytokines. Among them, interferon-γ (IFN-γ) was found to inhibit the over-expression of cytokines in Th2 lymphocytes, especially the secretion of IL-4 to lower the proliferation of B cells. Besides, IFN-γ could stimulate the immune response of Th1 and repress the synthesis of IgE (Sareneva T et al., Influenza A virus-induced IFN-α/β and IL-18 synergistically enhance IFN-γ gene expression in human T cells. *J Immunol* 160:6032-6038, 1998; Shida K et al., Lactobacillus casei inhibits antigen-induced IgE secretion through regulation of cytokine production in murine splenocyte culture. *Int Arch Allergy Immunol* 115:278-287, 1998). Since IFN-γ can repress B cell proliferation and IgE secretion, it is believed that IFN-γ is effective in treating allergy.

Lactic acid bacteria, which are gram-positive bacteria, are commonly used in industrial food fermentations. In recent studies, lactic acid bacteria were shown to stimulate IFN-γ secretion of cells (Blum S et al., Intensinal microflora and the interaction with immunocompetent cells. *Antonie Van Leeuwenhoek* 67:199-205, 1999; Contractor NV et al., Lymphoid hyperplasia, autoimmunity and compromised intestinal intraepithelial lymphocyte development in colits-free gnotobiotic IL-2-deficient mice. *J Immunol* 160:385-394, 1998; Delneste Y et al., Functional foods: Mechanism of action on immuncompetent cells. *Nutr Rev* 56:593-98, 1998; Haller D et al., Non-pathogenic bacteria elicit a different cytokine response by intestinal epithelial cell/leucocyte co-culture. *Gut* 47:79-87, 2000). Some specific lactic acid bacteria, such as Bifidobacterium lactis and Lactobacillus brevis subsp., were found to stimulate IFN-γ secretion of lymphocytes in blood derived from mice and humans (Arunachalam K et al., Enhancement of natural immune function by dietary consumption of Bifidobacterium lactis (HN 019). *Eur J Clin Nutr* 54:1-5, 2000; Kishi A et al., Effect of the oral administration of Lactobacillus brevis subsp. Coagulans on interferon-α producing capacity in humans. *J Am Coll Nutr* 15:408-412, 1996). It was also reported that lactic acid bacteria could stimulate lymphocytes derived from humans or mice to secret Interleukin-12 (IL-12), which was a T cell stimulatory cytokine activating T cells and NK cells to secrete IFN-γ (Pouwels P H et al., The potential of Lactobacillus as a carrier for oral immunization: development and preliminary characterization of vector systems for targeted delivery of antigens. *J Biotechnol* 44:183-92, 1996).

A topic dermatitis is one of the most common allergic diseases in children. The conventional method for treating a topic dermatitis is topic steroid therapy. However, the symptoms persist and recur frequently after stopping administrating steroids. Probiotic therapy is regarded as a safer and more effective way to treat a topic dermatitis. Some lactic acid bacteria were suggested to be effective in prevention and/or treatment of a topic dermatitis, such as L. rhamnosus strain GG (Kalliomaki, M., S. Salminen, et al., Probiotics and prevention of a topic disease: 4-year follow-up of a randomised placebo-controlled trial. *Lancet* 361(9372): 1869-71, 2003; Kirjavainen, P. V., S. J. Salminen, et al., Probiotic bacteria in the management of a topic disease: underscoring the importance of viability. *J Pediatr Gastroenterol Nutr* 36(2): 223-7, 2003; Dreborg, S., The implications of nomenclature. *Ann Allergy Asthma Immunol* 89(6 Suppl 1): 83-5, 2002; Pessi, T., Y. Sutas, et al., Interleukin-10 generation in a topic children following oral Lactobacillus rhamnosus GG. *Clin Exp Allergy* 30(12): 1804-8, 2000; Isolauri, E., T. Arvola, et al., Probiotics in the management of a topic eczema. *Clin Exp Allergy* 30(11): 1604-10, 2000), the combination of L. rhamnosus 19070-2 and L. reuteri DSM 122460 (Rosenfeldt, V., E. Benfeldt, et al., Effect of probiotic Lactobacillus strains in children with a topic dermatitis. *J Allergy Clin Immunol* 111(2): 389-95, 2003), and Bifidobacterium lactis Bb-12 (Isolauri, E., T. Arvola, et al., 2000).

SUMMARY OF THE INVENTION

The invention provides a novel microorganism strain, Lactobacillus fermentum GM-090.

In another aspect, the invention provides a method for stimulating IFN-γ secretion in a subject comprising administrating said subject with a composition comprising the microorganism strain, Lactobacillus fermentum GM-090.

In still another aspect, the invention provides a method for treating allergy in a subject comprising administrating said subject with a composition comprising the microorganism strain, *Lactobacillus fermentum* GM-090.

DETAILED DESCRIPTION OF THE INVENTION

The invention provides a novel microorganism strain, *Lactobacillus fermentum* GM-090, which is capable of stimulating IFN-γ secretion and/or treating allergy. The strain GM-090 was deposited on Jul. 19, 2004 with the China Center for Type Culture Collection (CCTCC) under the accession number of CCTCC M 204055.

The *Lactobacillus fermentum* GM-090 was isolated from human gastrointestinal tract.

The mycological characteristics of the *Lactobacillus fermentum* GM-090 are shown below:

(a) Morphological Characteristics:

(1) Shape and size of cell: bacillus, which has a rod-like shape with round edge when the cells after cultured at 37° C. overnight in MRS broth were observed with a microscope.

(2) Motility: non-motile (3) Flagella: none (4) Sporulation: no spore-forming (5) Gram-stain: positive (b) Cultural Characteristics:

(1) Medium: MRS broth (DIFCO® 0881) (as shown in Table 1), final pH 6.5±0.2

TABLE 1

| Component | G/L |
| --- | --- |
| Proteose peptone | 10.0 |
| Beef Extract | 10.0 |
| Yeast Extract | 5.0 |
| Dextrose | 20.0 |
| Polysorbate 80 | 1.0 |
| Ammonium Citrate | 2.0 |
| Sodium Acetate | 5.0 |
| Magnesium Sulfate | 0.1 |
| Manganese Sulfate | 0.05 |
| Dipotassium Phosphate | 2.0 |

(2) Cultural condition: 37° C. anaerobic (c) Physiological Characteristics:

(1) API 50 CHL test: API 50 CHL system is used for identification of lactic acid bacteria. By assaying the responses of a serious of enzymes, the characters of the lactic acid are established. Identification of the strain GM-090 was carried out by a carbohydrate fermentation test using API 50 CH strips and an API 50 CHL medium (API® Systems SA, Montalieu Vercieu, France)The result of API 50 CHL test of GM-090 is listed in Table 2;

TABLE 2

| 0 | − | GLY | − | ERY | − | DARA | − | LARA | − | RIB | + | DXYL | + | LXYL | − | ADO | − | MDX | − | GAL | + |
| --- | --- | --- | --- | --- | --- | --- | --- | --- | --- | --- | --- | --- | --- | --- | --- | --- | --- | --- | --- | --- | --- |
| GLU | + | FRU | + | MNE | + | SBE | − | RHA | − | DUL | − | INO | − | MAN | − | SOR | − | MDM | − | MDG | − |
| NAG | − | AMY | − | ARB | − | ESC | − | SAL | − | CEL | − | MAL | + | LAC | + | MEL | + | SAC | − | TRE | − |
| INU | − | MLZ | − | RAF | + | AMD | − | GLYG | − | XLT | − | GEN | − | TUR | − | LYX | − | TAG | − | D-FUC | − |
| LFUC | − | DARL | − | LARL | − | GNT | + | 2KG | − | 5KG | − | | | | | | | | | | |

| | % Id | T | Tests against | |
| --- | --- | --- | --- | --- |
| Significant taxa | | | | |
| *L. fermentum* | 99.9 | 0.92 | 1 | |
| Next choice | | | | |
| *L. brevis* | 0.1 | 0.55 | 3 | |
| *L. fermentum* SACCHAROSE | | 1 test(s) (SAC) | against 86% | |

TABLE 2-continued

Next choice

| L. brevis | 2:3 test (s) | against |
|---|---|---|
| L-ARABINOSE | (LARA) | 99% |
| SACCHAROSE | (SAC) | 93% |
| D-MANNOSE | (MNE) | 7% |

(d) Genetic Characteristics:

The *Lactobacillus* species specific primers were used to identify the species of the strain GM-090 according to Yeung et al (Yeung, P. S. M., Sanders, M. E., Kitts, C. L., Cano, R., Tong, P. S., Species-specific Identification of Commercial Probiotic Strains. *J. Diary. Sci.* 85:1039-1051, 2002). The 16s rDNA sequence is as shown in SEQ ID NO: 1. Also, randomly amplified polymorphic DNA (RAPD analysis) was performed. It shows that GM-090 belongs to *Lactobacillus fermentum*, but has a specific RAPD patterns. Given the above, GM-090 is a novel *Lactobacillus fermentum* strain.

Figure 4:
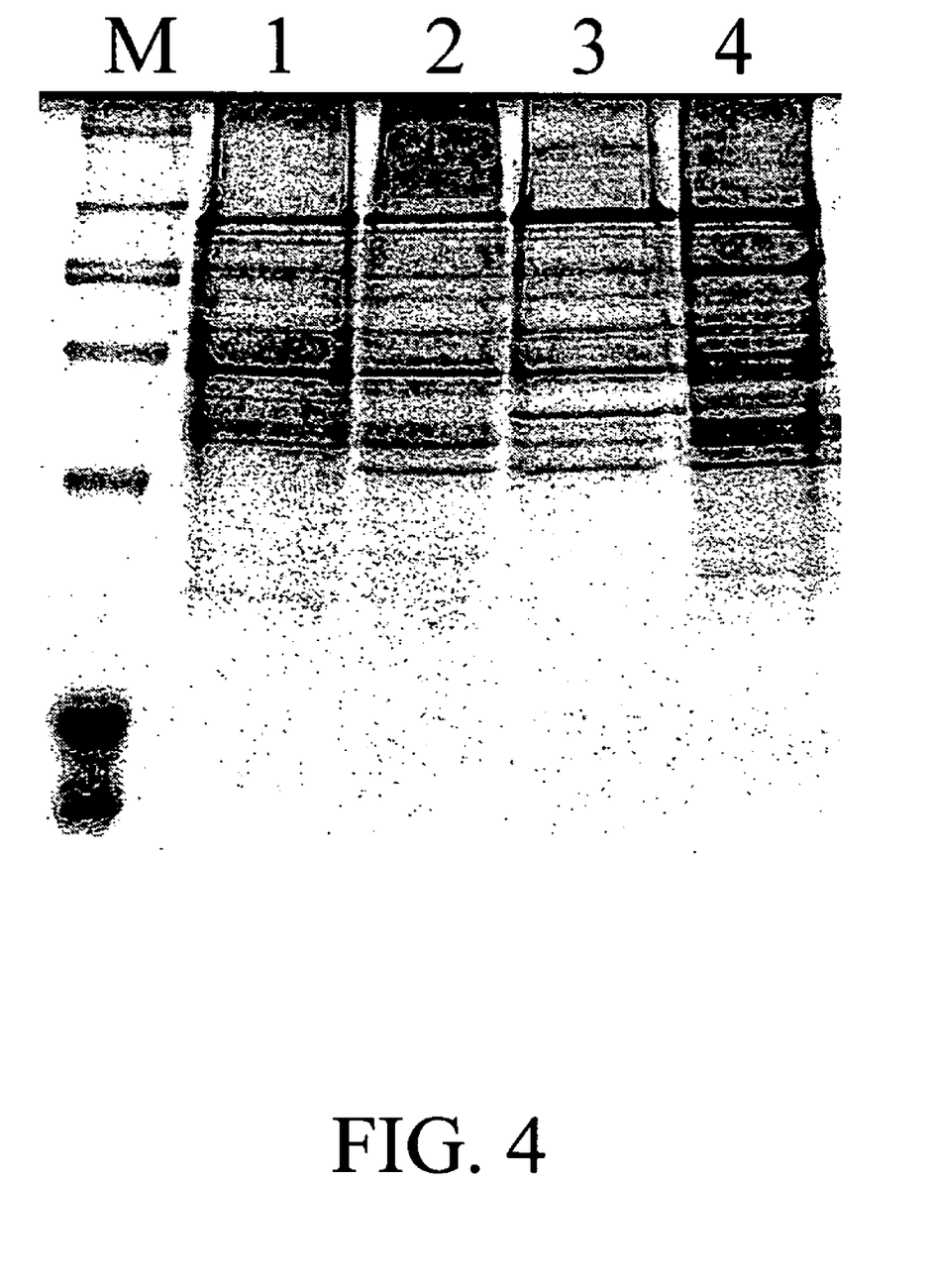
FIG. 4 illustrates SDS-PAGE patterns of cell wall proteins from various strains of *Lactobacillus fermentum*. M, protein marker (Lane 1, *Lactobacillus fermentum* GM-090; Lane 2, *Lactobacillus fermentum* ATCC 9338; Lane 3, *Lactobacillus fermentum* ATCC 11739 and Lane 4, *Lactobacillus fermentum* ATCC 14931).

(e) Cell wall proteins of the strain GM-090:

The cell wall proteins of the strain GM-090 show specific pattern when compared with other conventional *Lactobacillus fermentum* strains. The SDS-PAGE patterns of the cell wall proteins of the strain GM-090 are shown in FIG. 4.

The present invention provides a method for stimulating IFN-γ secretion and/or treating allergy in a subject comprising administrating said subject with a composition comprising the strain GM-090.

*L. fermentum* is usually found during malt whisky fermentation (van Beek, S. and Pries, F. G. Evolution of the lactic acid bacterial community during malt whisky fermentation: a polyphasic study. *Appl Environ Microbiol* 68(1): 297-305, 2002; and Simpson, K. L. et al., Characterization of lactobacilli from Scotch malt whisky distilleries and description of *Lactobacillus ferintoshensis* sp. nov., a new species isolated from malt whisky fermentations. *Microbiology* 147: 1007-1016, 2001). Intravenous injection of saline washed *L. fermentum* was shown to elicit hypersensitivity reactions in rabbits (Jackson, D. E., C. R. Howlett, et al., Induction of hypersensitivity reactions to *Lactobacillus fermentum* and lipoteichoic acid in rabbits. Part II. *Int Arch Allergy Appl Immunol* 65(3): 304-12, 1981; Jackson, D. E., G. D. Jackson, et al., Induction of IgM immunological memory to lipoteichoic acids in rabbits. Part I. *Int Arch Allergy Appl Immunol* 65(2): 198-202, 1981; Jackson, D. E., A. J. Wicken, et al., Immune responses to lipoteichoic acid: comparison of antibody responses in rabbits and mice. Part II. *Int Arch Allergy Appl Immunol* 65(2): 203-11, 1981). On the other hand, one strain, *L. fermentum* CP34 was found to have the significant effect of decreasing the serum antigen-specific IgE levels compared to a control group (Ishida, Y. et al., Decrease in ovalbumin specific IgE of mice serum after oral uptake of lactic acid bacteria. *Biosci Biotechnol Biochem* 67(5): 951-957, 2003).

It is surprisingly found in the invention that the strain GM-090 has ability to stimulate IFN-γ secretion. In the animal model of the invention, the splenocytes cultured with the strain GM-090 were stimulated to increase IFN-γ secretion. The effect of GM-090 in stimulating IFN-γ secretion is even better than the positive control, PHA.

According to the invention, *L. fermentum* is for treating allergy in a subject. Preferably, the allergy is preferably dermatitis. More preferably, the dermatitis is a topic dermatitis. The term "allergy" used herein refers to IFN-γ mediated allergy. The allergic disorders include rhinitis, sinusitis, asthma, hypersensitive pneumonia, extrinsic allergic alveolitis, conjunctivitis, urticaria, eczema, dermatitis, anaphylaxis, angioedema, allergic and migraine headache, and certain gastrointestinal disorders.

According to the examples of the invention, the conditions of dermatitis were dramatically improved by treating with GM-090. Furthermore, the symptom is nearly dispelled.

According to the invention, the lactic acid bacterial strain can be live or inactive. For instance, the live bacterial strains can be treated by a heating step, or other treatments commonly used in the art for killing the lactic acid bacterial strains to obtain inactive strains. Preferably, the lactic acid bacterial is lyophilized.

In another aspect, the invention provides a composition comprising the strain *L. fermentum* GM-090.

According to the invention, the lactic acid bacterial strain can be included in a pharmaceutical composition, dietary supplement, food, healthy food, medical food, or the components thereof, which are normally administered by people. In a preferred embodiment of the invention, the lactic acid bacterial strain can be delivered in food form, such as in a coagulated milk product that prepared through the fermentation of a lactic acid bacterium in milk. The food products prepared thus can be conveniently administrated to infants or children.

In still another aspect, the invention provides a method for stimulating IFN-γ secretion in a subject comprising administrating said subject with a composition comprising the isolated strain *L. fermentum* GM-090.

In still another aspect, the invention provides a method for treating allergy in a subject comprising administrating said subject with a composition comprising the isolated strain GM-090.

The following Examples are given for the purpose of illustration only and are not intended to limit the scope of the present invention.

EXAMPLE 1

Isolation of *Lactobacillus fermentum* GM-090

A piece of human stomach tissue taken by an endoscope was cultured in 2 mL of *Lactobacillus MRS Broth (DIFCO®* 0881). The broth containing the tissue was plated on *Lactobacillus selective agar* and incubated at 37° C. for one day. Single colony growing on the plate was selected and subjected to Gram-stain. Gram-positive bacteria were then selected. One strain, called as *Lactobacillus fermentum* GM-090, was cloned.

EXAMPLE 2

Gram Stain

Gram staining was performed according to manuscript of Gram-color staining set for Gram stain (MERCK®, Darmstadt, Germany). The bacteria were first stained with crystal violet for 1 min, and then treated with Lugol's solution for 1 min. The sample was carefully rinsed with distilled water for about 5 s. The slide was swirled for about 10-15 s in solution 3 or 4 for decolorisation solution. Swirling was stopped when no more dye was released and the smear appeared greyish-blue. The sample was carefully rinsed again with distilled water for about 5 s. The slide was completely covered with solution 5, safranin solution, for 1 min. The sample was carefully rinsed with distilled water for about 5 s. After the sample was dry, it was subject to examine under a microscopy.

Figure 1:
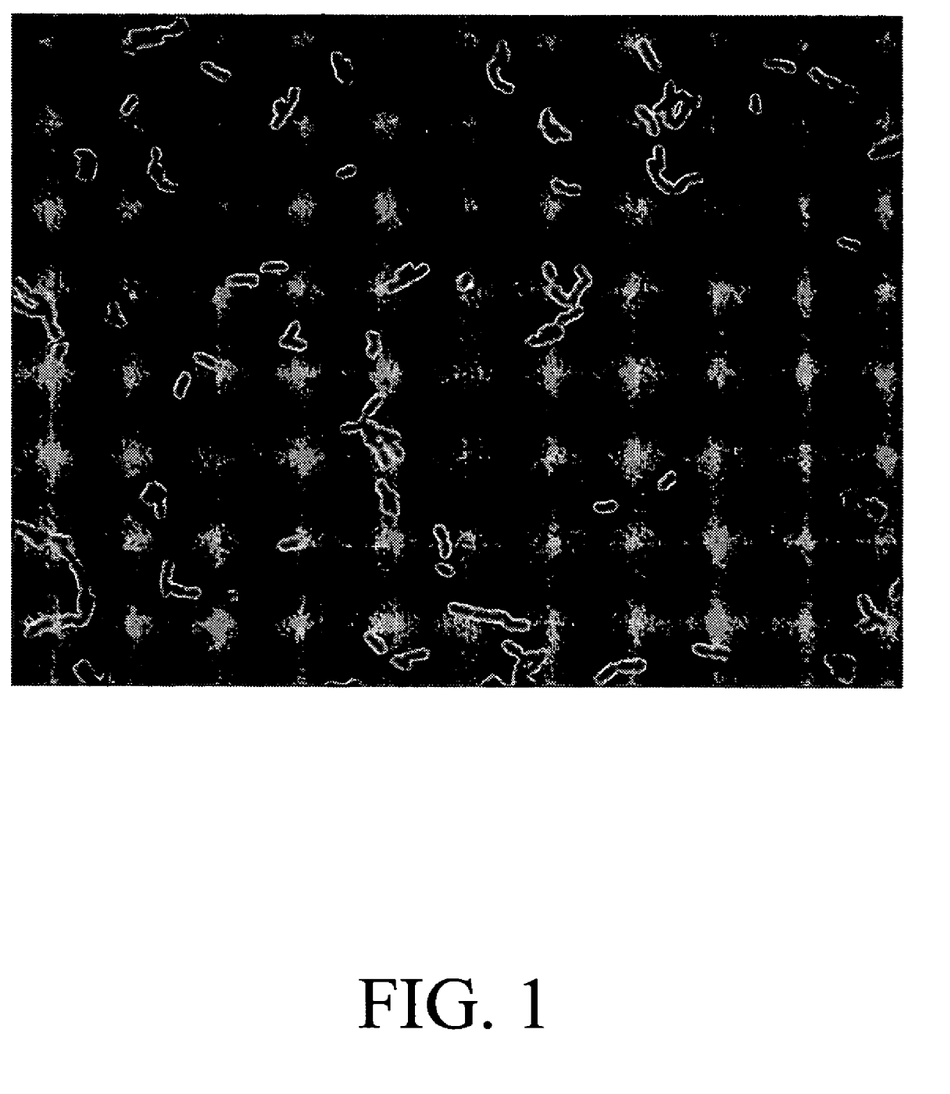
FIG. 1 illustrates the 1000× microscopic view of GM-090.

The result of examining under a microscopy was shown in FIG. 1.

EXAMPLE 3

16s rDNA Sequence Determination

The *Lactobacillus* species specific primers were used to identify the species of the strain GM-090 according to Yeung et al (2002). Briefly, the primers PAF (5'-AGA GTT TGA TCC TGG CTC AG-3', SEQ ID NO: 2) and 536R (5'-GTA TTA CCG CGG CTG CTG-3', SEQ ID NO: 3) were used to amplify the 5' region of the 16S rDNA gene. PCR was performed in an iCycler (Bio-Rad® Laboratories Inc.). The amplification was programmed as follows: preincubation at 94° C. for 2 min, followed by 40 cycles at: 94° C. for 45 s, 55° C. for 45 s, and 72° C. for 60 s. After these cycles, the reaction was maintained at 72° C. for 7 min and then cooled to 4° C. The PCR product was separated on a 1.5% agarose gel, eluted and auto sequenced. The oligonucleotide sequences were used to search the GenBank (National Center of Biotechnology information, www.ncbi.nlm.nih.gov) for homologous sequences.

The sequence of 16s rDNA of GM-090 was identical to that of *L. fermentum* strain PL 9006 16S ribosomal RNA gene.

EXAMPLE 4

Randomly Amplified Polymorphic DNA (RAPD Analysis

Randomly amplified polymorphic DNA (RAPD) analysis was used to distinguish the strain GM-090 from other *Lactobacillus fermentum* strains according to Angelis et al (Angelis, M. D., Corsetti, A., Tosti, N., Rossi, J., Corbo, M. R., and Gobbetti, M., Characterization of Non-Starter Lactic Acid Bacteria from Italian Ewe Cheeses Based on Phenotypic, Genotypic, and Cell Wall Protein Analyses. *Appl. Environ. Microbiol.* 67: 2011-2020, 2001). Two primers, P2 (5'-ATG TAA CGC C-3', SEQ ID NO: 4) and P3 (5'-CTG CGG CAT-3', SEQ ID NO: 5) were used. PCR was performed in an iCycler (Bio-Rad® Laboratories Inc.). The PCR program comprised 45 cycles of denaturation for 1 min at 94° C., annealing for 1 min at 35° C., and extension for 2 min at 72° C.; the cycles were preceded by denaturation at 94° C. for 4 min and were followed by extension at 72° C. for 5 min. PCR products were separated by electrophoresis on a 1.5% (wt/vol) agarose gel, and the DNA was detected by UV transillumination after staining with ethidium bromide (0.5 mg/ml).

Figure 2:
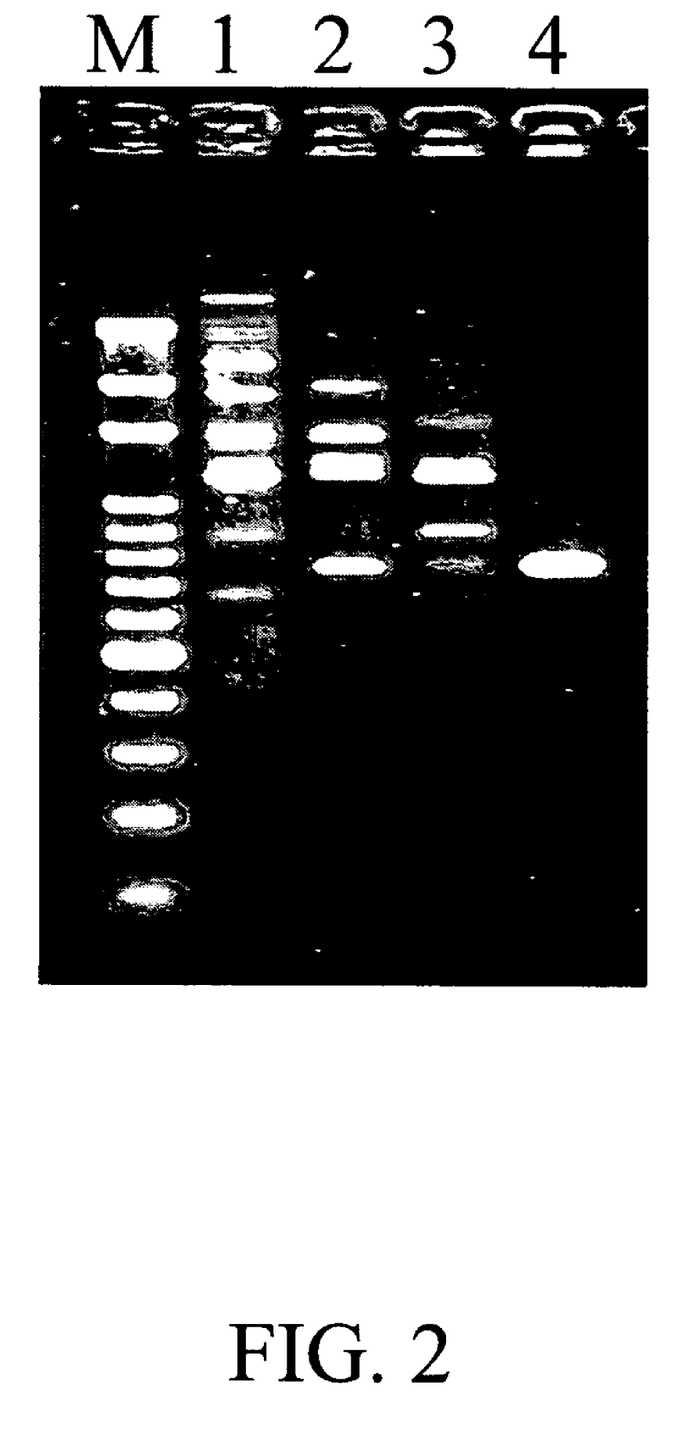
FIG. 2 illustrates RAPD patterns obtained with primers P2 of various strains of *Lactobacillus fermentum*. M, 100 bps DNA marker (Lane 1, *Lactobacillus fermentum* GM-090; Lane 2, *Lactobacillus fermentum* ATCC 9338; Lane 3, *Lactobacillus fermentum* ATCC 11739 and Lane 4, *Lactobacillus fermentum* ATCC 14931).
Figure 3:
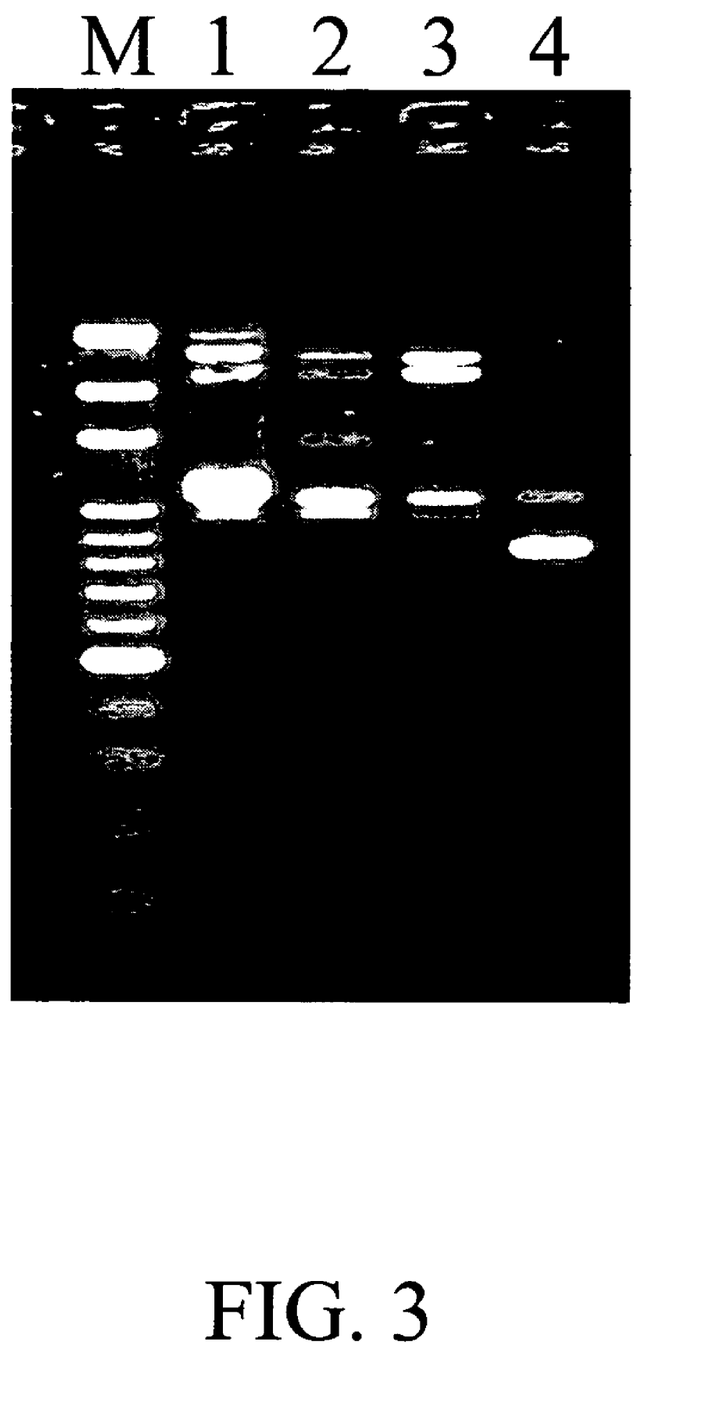
FIG. 3 illustrates RAPD patterns obtained with primers P3 of various strains of *Lactobacillus fermentum*. M, 100 bps DNA marker (Lane 1, *Lactobacillus fermentum* GM-090; Lane 2, *Lactobacillus fermentum* ATCC 9338; Lane 3, *Lactobacillus fermentum* ATCC 11739 and Lane 4, *Lactobacillus fermentum* ATCC 14931).

The result of RAPD patterns obtained with primers P2 was shown in FIG. 2, and the result of RAPD patterns obtained with primers P3 was shown in FIG. 3. It evidenced that the RAPD patterns of GM-090 were different from those of conventional *L. fermentum* strains. Given the above, GM-090 was a novel *Lactobacillus fermentum* strain.

EXAMPLE 5

Cell Wall Proteins Extraction and Analysis of GM-090

Cell wall protein was extracted according to Angelis et al (2001). Briefly, Twenty-four-hour-old cells of mesophilic lactobacilli cultivated in MRS broth were harvested, washed twice in 0.05 M Tris-HCl (pH 7.5) containing 0.1 M $CaCl_2$, and resuspended in 1 ml of the same buffer at an $A_{600}$ of 10.0. After centrifugation at 8,000×g for 5 min, cell wall proteins were extracted from the pellets with 1.0 ml of extraction buffer (pH 8.0) containing 0.01 M EDTA, 0.01 M NaCl, and 2%(wt/vol) SDS. Suspensions were stored at room temperature for 60 min, heated at 100° C. for 5 min, and centrifuged at 11,600×g for 10 min at 4□° C. The supernatants were analyzed by SDS-PAGE and stained with Comassie blue.

The result was shown in FIG. 4. GM-090 was evidenced to be one strain of *Lactobacillus fermentum*.

EXAMPLE 6

GM-090 for Stimulating IFN-γ

To measure cytokine production by mouse splenocytes, the mouse spleen cells were harvested from BALB/c mice and cultured in RPMI 1640 medium (GIBCO/BRL®, Gaithersburg, Md., USA) supplemented with 10% fetal calf serum. One hundred microliters of cell suspension ($4 \times 10^5$ cells/ml) was added to 96 well-plated and incubated without (naïve) or with various strains of *lactobacilli*. Ten μg/ml PHA (Sigma®, St. Louis, Mo., USA) was used as positive control. The microplates were incubated at 37° C. in a humidified atmosphere of 5% $CO_2$ for 48 hours. The levels of IFN-γ in splenocyte culture supernatants were determined by ELISA with commercial kits (OptEIA Mouse IFN-γ Set, BD Biosciences Pharmingen, San Diego, Calif., USA).

Figure 5:
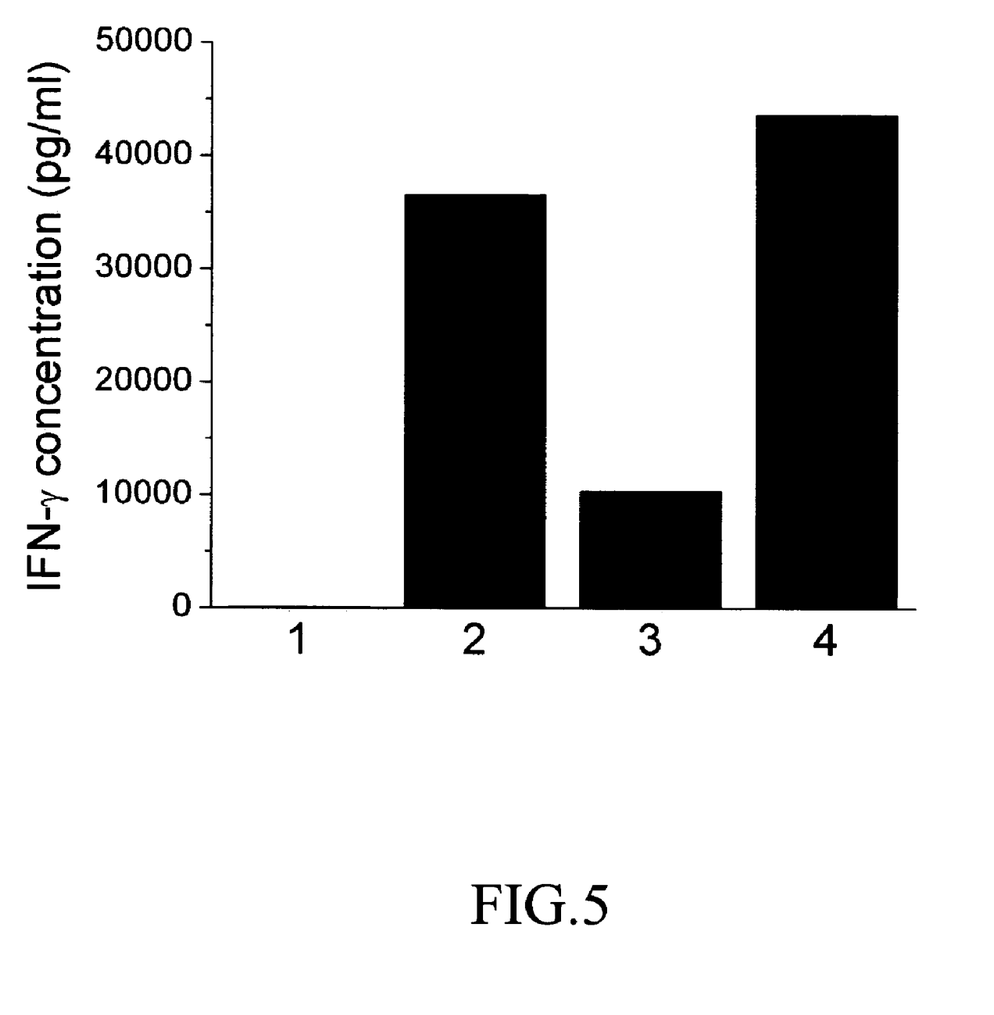
FIG. 5 illustrates the effects of PHA, *Lactobacillus paracasei* and *Lactobacillus fermentum* on stimulation of IFN-γ production by mouse splenocytes (Lane 1, naive; Lane 2, PHA; Lane 3, *Lactobacillus paracasei*; Lane 4, *Lactobacillus fermentum* GM-090).

The result was shown in FIG. 5. GM-090 was evidenced to stimulate IFN-γ secretion more strongly than the positive control PHA.

EXAMPLE 7

GM-090 for Treating Allergy (1)

A 6-year-old girl was initially diagnosed as atopic dermatitis when she was 3 month old. Eczematous manifestation was noted over the face at that time. The symptoms worsted afterwards with secondary infection. The initial culture showed *staphylococcus aureus*. After 7-day antibiotic therapy, she received hydrolyzed infant formulae feeding. However, several infection attacks still happened during past 5 years. In addition, lichenification and eczematous changes were both noted over face and flexure area of extremities. Though she visited several famous dermatologists in medical centers, symptoms persisted and recurred frequently. Topic steroid therapy was effective in this case. But symptoms recurred once she discontinued steroid therapy. The clinical doctor measured her IgE level (immunoglobulin (Ig) E: Total IgE 1120 IU/ml, Mite-specific IgE>100 KU/ml).

Lyophilized GM-090 were administrated $2\times10^9$ CFU/day.

Figure 6A:
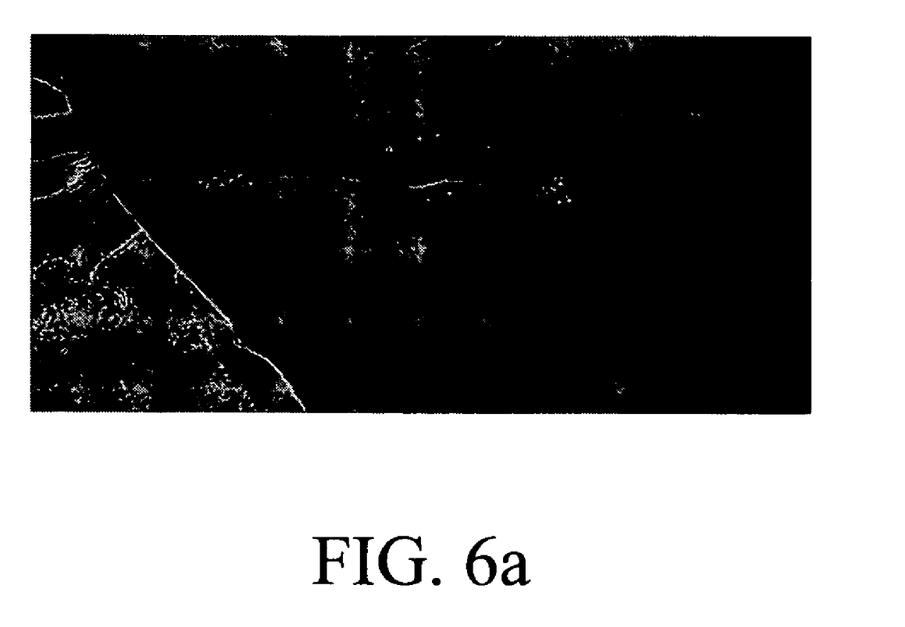
FIG. 6 illustrates the pictures of the patient described in Example 7 (a: before treatment. b: after treatment).
Figure 6B:
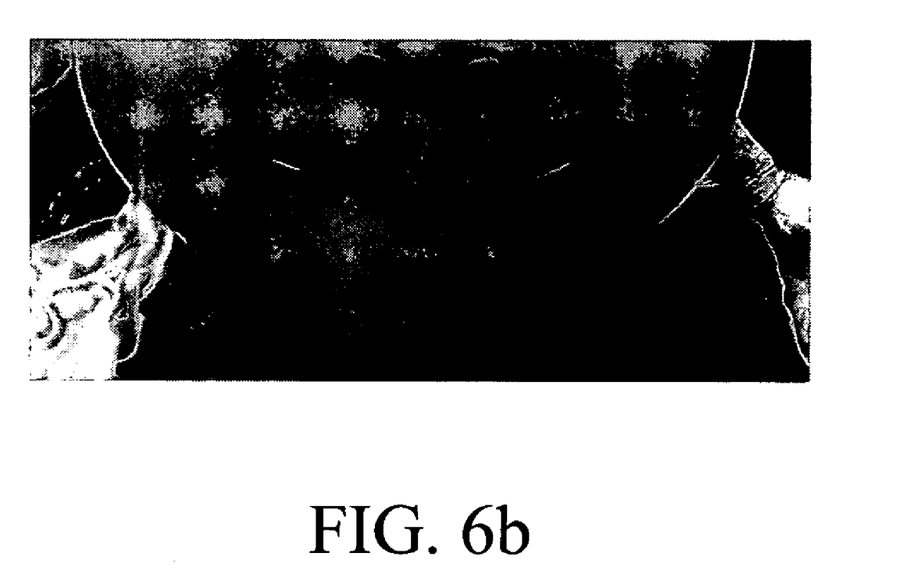
Figure 7A:
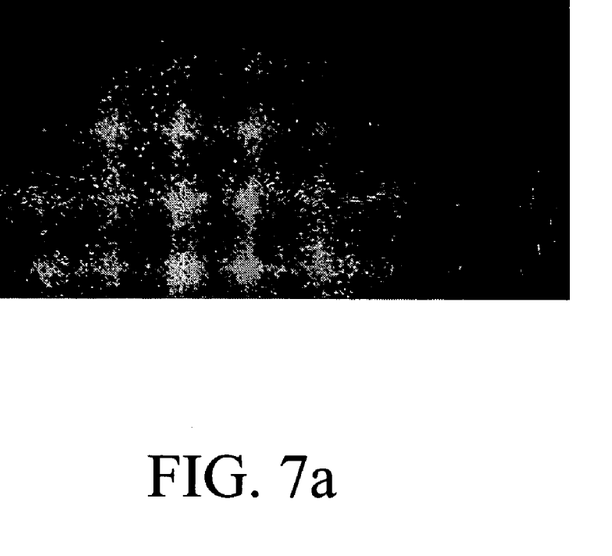
FIG. 7 illustrates the pictures of the patient described in Example 7 (a: before treatment. b: after treatment).
Figure 7B:
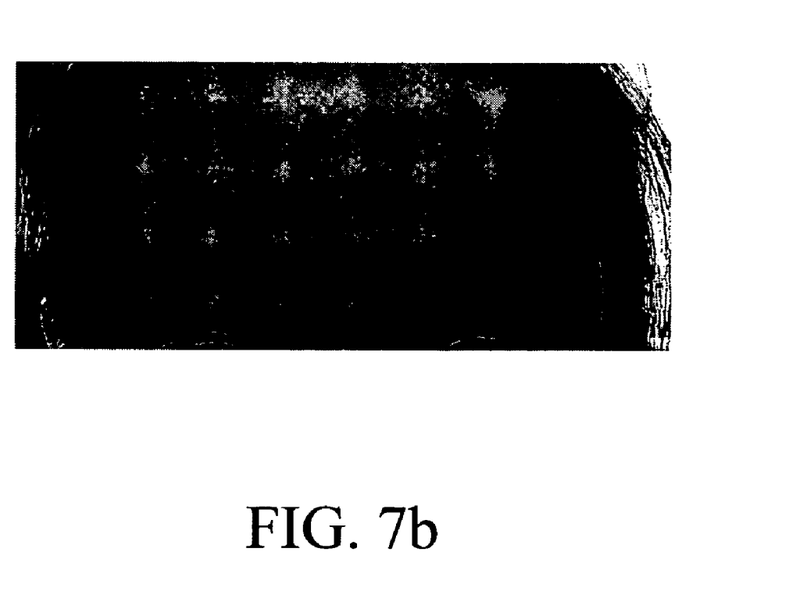

After three weeks, the symptom has already been dispelled. The pictures of the patient were shown in FIGS. 6 and 7.

EXAMPLE 8

GM-090 for Treating Allergy (2)

When the patient was on her primary school period, she frequently got the system of stuffy nose, and itching eyes whenever getting up. It began with probably five years, some erythmatous rash was noted over her face, neck, four limbs. Some skin even presents lichenification. Although she visited dermatologists all over and treated with steroids, the condition just improved slightly, and got worsen promptly soon after stopping taking medicines (steroids). She has received protopic therapy during past 1 year. Though symptoms can be controlled by this therapy, she looked for alternative therapy. Her parents all had anaphylaxis rhinitis medical history in family's history.

Lyophilized GM-090 was taken before meal in the morning and evening.

Figure 8A:
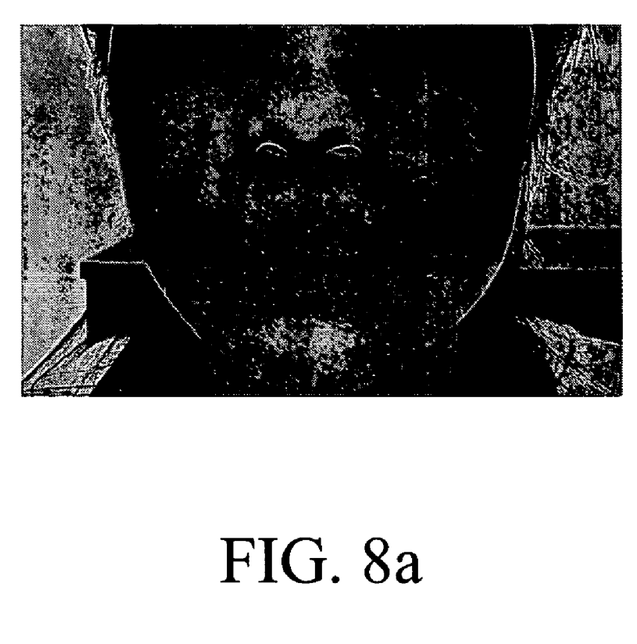
FIG. 8 illustrates the pictures of the patient described in Example 8 (a: before treatment. b: after treatment).
Figure 8B:
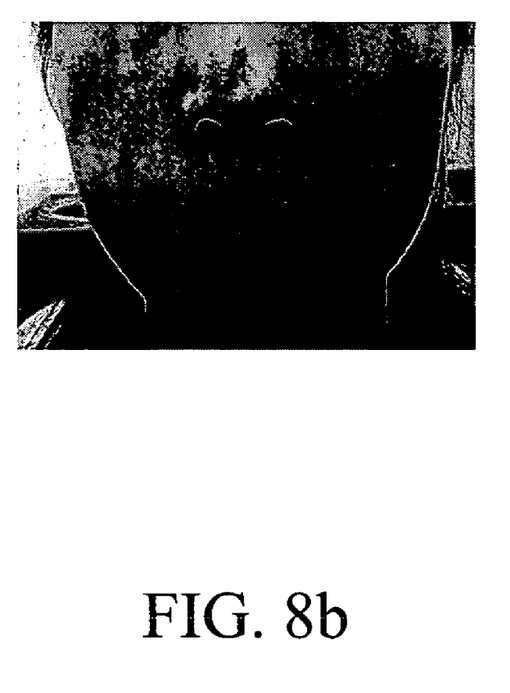

After 14-day therapy, the condition was greatly improved, and the symptom has nearly been dispelled. (Immunoglobulin (Ig) E measures the data clinically: Total IgE 580 IU/ml, Mite-specific IgE>50KU/ml). The pictures were shown in FIG. 8.

While embodiments of the present invention have been illustrated and described, various modifications and improvements can be made by persons skilled in the art. It is intended that the present invention is not limited to the particular forms as illustrated, and that all the modifications not departing from the spirit and scope of the present invention are within the scope as defined in the appended claims.

---

What is claimed is:

1. An isolated microorganism of strain, *Lactobacillus fermentum* GM-090, deposited at the China Center for Type Culture Collection under the accession number of CCTCC M 204055.

2. A composition comprising an isolated microorganism of strain *Lactobacillus fermentum* GM-090, deposited at the China Center for Type Culture Collection under the accession number of CCTCC M 204055.

3. The composition of claim 2, wherein the microorganism is live.

4. The composition of claim 2, wherein the microorganism is inactivated.

5. The composition of claim 2, wherein the microorganism is lyophilized.

6. The composition of claim 2 which is packaged as of a pharmaceutical composition, dietary supplement, health food, medical food, or a component of any of the foregoing.

7. The composition of claim 2 further comprising a coagulated milk product.

* * * * *